United States Patent [19]

Divilio et al.

[11] Patent Number: 5,417,655
[45] Date of Patent: May 23, 1995

[54] ATTACHMENT FOR REMOVAL OF SMOKE IN LAPAROSCOPIC SURGERY

[76] Inventors: Robert J. Divilio, 10015 Brookmoor Dr., Silver Spring, Md. 20901; L. Thomas Divilio, P.O. Box 822, Easton, Md. 21601

[21] Appl. No.: 234,120

[22] Filed: Apr. 28, 1994

Related U.S. Application Data

[62] Division of Ser. No. 27,503, Mar. 2, 1993, Pat. No. 5,336,169.

[51] Int. Cl.$^6$ .............................................. A61M 31/00
[52] U.S. Cl. ........................................ 604/22; 604/49; 604/319
[58] Field of Search ................ 604/21, 22, 19, 20, 604/313, 319, 35, 45, 51, 49; 606/5, 10, 14, 15, 34, 19, 46, 47, 32, 37

[56] References Cited

U.S. PATENT DOCUMENTS

| | | |
|---|---|---|
| 3,982,541 | 9/1976 | L'esperance, Jr. . |
| 4,735,603 | 4/1988 | Goodson et al. . |
| 5,047,072 | 9/1991 | Wertz et al. . |
| 5,055,100 | 10/1991 | Olsen . |
| 5,058,570 | 10/1991 | Idemoto et al. . |
| 5,181,916 | 1/1993 | Reynolds et al. . |
| 5,192,267 | 3/1993 | Shapia et al. . |
| 5,192,276 | 3/1993 | Gatti . |
| 5,209,747 | 5/1993 | Knoepfler . |
| 5,211,639 | 5/1993 | Wilk . |
| 5,215,539 | 6/1993 | Schoolman . |
| 5,264,026 | 11/1993 | Paul . |
| 5,267,955 | 12/1993 | Hanson . |
| 5,318,518 | 6/1994 | Plechingen et al. . |
| 5,378,150 | 1/1995 | Harrel . |

Primary Examiner—C. Fred Rosenbaum
Assistant Examiner—Perry E. Van Over
Attorney, Agent, or Firm—Leander F. Aulisio

[57] ABSTRACT

A twist-on attachment for laparoscopic port for withdrawal of smoke and other contaminants from a patient cavity during laparoscopic surgery to provide an atmosphere of enhanced air quality and improved visibility for the surgeon.

8 Claims, 2 Drawing Sheets

ATTACHMENT FOR REMOVAL OF SMOKE IN LAPAROSCOPIC SURGERY

This application is filed as a divisional application of application Ser. No. 08/027,503, filed Mar. 2, 1993, now U.S. Pat. No. 5,336,169.

FIELD OF THE INVENTION

The invention relates to surgical procedures and specifically relates to a device and method for obtaining a smoke-free environment at an operation site in a patient cavity during laparoscopy.

BACKGROUND OF THE INVENTION

The use of laparoscopic surgical procedures has increased dramatically in recent years. All of these procedures include the following basic steps: passing a small diameter cylindrical port through the abdominal wall, inflating the abdomen with a gas such as carbon dioxide, and passing surgical instruments through the port and into the abdomen. Optical fibers can be passed through the port and the surgical procedures can be monitored on a television screen. Surgical cutting and cauterizing can be performed with an electrosurgical instrument or a focused laser beam, typically from a $CO_2$ laser. In laser laparoscopy the laser beam,is transmitted in a laparoscopic port through the abdominal muscular wall of a patient into the abdominal cavity where the laser beam is used to excise or remove body tissue by vaporization. Laser laparoscopic surgical procedures are used to treat a number of gynecological problems including hydrosalpinx, endometriosis, small uterine fibroids, and pelvic adhesions. The only surgical opening required is a small incision though the abdominal wall because the laparoscopic port is small, typically about 12.7 mm in diameter. Use of this procedure avoids the risk of laparotomy requiring full size abdominal incisions.

With the rapid expansion in the use of a lasers as surgical instruments, new problems have been encountered which have not been confronted in conventional surgery. One such problem is that of the smoke or laser plume produced during laser surgery. While some smoke may be produced by conventional electric scalpels and similar devices, the intensity and volume of the smoke and pollutants produced in laser surgery presents a problem of a much larger magnitude.

The high intensity of lasers used in laser surgery causes oxidation of tissue and fluid contacted by the laser. This typically results in a dense laser plume emitted from the surgical site. The laser plume contains a variety of hydrocarbon compounds, carbon monoxide, moisture, and unpleasant odors. It is also now conjectured that the laser plume may contain quantities of biologically viable material, which could range in content from relatively benign organisms to cancerous and deadly viral materials.

In one study which sought to determine the scope and intensity of the smoke produced during surgery, tissue was contacted by a laser under controlled conditions. It was found that the smoke and particulate matter produced a density approximately 52 times greater than the recommended density set by the governmental regulatory agencies.

In addition, the laser plume is known to contain particles of varying sizes. For example, one investigation found particles varying in size from under 0.4 microns to over 9.0 microns. Nevertheless, a large portion of the particles found in that study were under 1.1 microns in size which are capable of being easily deposited in the alveoli of the lungs. Not only are particles of this size irritating to the respiratory system, but they may also be capable of causing serious respiratory disease. Repeated exposure to such particles can build deposits within the lungs.

Several investigators have pointed out that repeated exposure to laser plumes may result in pneumonitis. In addition, it has been found that the laser plume may be mutagenic, and thus possibly carcinogenic. The presence of biologically viable materials poses the risk of the spread of contagions. While much of the data in this area is still not definitive, it is clear that direct contact with laser plume presents significant health risks, particularly to exposed medical personnel and patients.

Laser plumes present additional difficulties. For example, it has been found that the laser plumes condense on the optical components of the laparoscope itself, thereby impairing visibility or causing pitting damage to lenses. Similarly, the laser plume may enter and clog mechanical devices and filters located in the operating room.

In order to combat the problems of damage to the laser itself, many conventional laser systems are equipped with air circulation systems. These systems drive a stream of air over the sensitive laser equipment and the area being contacted by the laser beam. While the laser plume is thus driven away from the laser equipment, it is forced into the ambient air, making it more difficult to control laser plume emissions.

Also, the superheated steam component of the laser plume may cause serious burns in the event of contact with flesh. Of course, the primary danger in this regard is to the patient. The steam is produced by vaporizing irrigation or body fluids, and there is a danger that those vaporized fluids may contact the surrounding tissue.

When the steam does leave the localized surgical site, there is a danger that the heat may cause discomfort or otherwise provide an undesirable distraction to the surgeon or other operating room personnel. Thus, it is controlled and removed from the surgical site before it injures the tissues surrounding the surgical site or becomes a problem to operating room personnel.

Good practice thus dictates that the laser plume be controlled and removed from the surgical site, and various devices have been developed for this purpose. Most involve the use of some form of suction.

The following patents outline the state of the art in laser smoke removal processes and vacuum line control systems. All of the patents are incorporated herein by reference.

U.S. Pat. No. 5,055,100 (Olsen) relates to a clip-on attachment for an electrosurgical instrument. A back end of the attachment, which includes a hollow tube, is adapted for connection to a source of low fluid pressure. A front end of the attachment is situated near the front end of the electrode for more efficient removal of smoke and other fluids.

U.S. Pat. No. 3,319,628 (Halligan) discloses a suction catheter regulator device formed of relatively rigid plastic material and having an integrally formed control tube extending transversely from a conduit tube. The control tube is provided with an outer open end with a flanged finger engaging piece surrounding the open end.

U.S. Pat. No. 3,982,541 (L'Esperance, Jr.) relates to an eye surgical instrument for performing laser surgery comprising a probe having a central tube disposed within an outer tube. The central tube is open at both ends with one end disposed within the probe and the other end exposed at a free end of the probe for contact with body tissue. A laser beam is directed through the central tube. A means is connected to the probe for removing smoke and vaporized portions of tissue through the space between the tubes in a direction away from the free end of the probe.

U.S. Pat. No. 5,047,072 (Wertz et al) discloses a portable system for evacuating laser smoke from a surgical site comprising a primary inlet tube supported on an articulated arm, a suction canister in communication with the primary inlet tube, a primary filter canister in connection with the suction canister by means of a secondary inlet tube, and a disposable prefilter disc. A fan, positioned downstream of the primary filter canister is employed for advancing laser smoke through the portable system.

U.S. Pat. No. 3,998,227 (Holbrook et al) discloses a regulator device for hospital vacuum systems comprising a base housing having an air outlet and means for providing a variable, atmospheric air inlet to the base house. The base housing has an air passageway means between air outlet and inlet of a transverse open cross-sectional area not greater than 0.002 square inches.

U.S. Pat. No. 4,735,603 (Goodson et al) discloses a laser smoke evacuation system for use with laser laparoscopic surgery. In a preferred embodiment, the $CO_2$ gas employed to distend the abdominal area of the patient is withdrawn in incremental amounts, purified by removal of laser smoke and returned to the patient cavity. A bacterial filter is also employed to remove microorganisms. An entire closed circuit $CO_2$ gas recirculation system is disclosed.

U.S. Pat. No. 3,834,388 (Sauer) discloses a suction control arrangement for a suction catheter, the control arrangement having an opening to the atmosphere which can be slidably opened or closed. When a slide is in the open position, the internal flow of the catheter is exposed to the atmosphere and the vacuum and suction force is eliminated thus preventing fluid flow out of any body cavities.

SUMMARY OF THE INVENTION

A need continues to exist for controlling the generation and removal of the plume associated with surgery which employs laser or electrocautery techniques.

To fill this need a device is proposed which will be referred to as an air quality enhancement device. A method is also proposed by which the generated plume is effectively removed. The device receives the plume generated during surgery and effectively traps it and removes it from the surgical site without any adverse effect on the surgical procedure.

In one aspect, the present invention provides a disposable suction attachment device for a laparoscopic port having a vent valve on the side thereof. The device dramatically improves the air quality of the operating room by preventing laser or cautery smoke from entering the atmosphere. In one embodiment, the device comprises,.a hollow envelope having at least one aperture disposed at a forward region thereof. The hollow envelope further has a first opening formed in the hollow envelope at a forward region thereof, and a second opening formed in the envelope at a rearward region thereof. A fluid flow tube is disposed within the envelope and is in sealing arrangement with the envelope at the first opening formed in the envelope. The fluid flow tube extends into the interior of the hollow envelope to at least a point immediately downstream of at least one aperture. A first connecting structure is located on the exterior of the envelope and is in a sealing arrangement with the envelope at the first opening formed in the envelope. A second connecting structure is located on the exterior of the envelope and is in a sealing arrangement with the envelope at the second opening formed in the envelope.

The device is connected to a laparoscopic port by joining a venting structure associated with the laparoscopic port to the device via the first connecting structure. Preferably the first connecting structure comprises a Luer lock for twist-on attachment. The second connecting structure, which is preferably a flexible plastic tube, allows for the device to directly engage a vacuum line such as the vacuum system built into the operating room or a portable vacuum system.

BRIEF DESCRIPTION OF THE DRAWINGS

The forgoing objects and advantages and preferred embodiments of the apparatus and method of the invention will be better understood from the following detailed description thereof taken in conjunction with the accompanying drawings wherein.

DETAILED DESCRIPTION OF THE PREFERRED EMBODIMENTS OF THE INVENTION

A variety of different laparoscopic ports are known in the art. These various laparoscopic ports are designed to allow visualization of the surgical field within the pelvis, access of the surgical instruments, and input of $CO_2$ gas to form the closed circuit flow removal of the laser or electrocautery smoke, and $CO_2$ gas and to insufflate and thus distend the abdomen by imposing and maintaining a steady state pressure within the abdomen. The pressure may range from plus 15 to 20 mm of mercury relative to atmospheric pressure. The insufflation and resulting abdominal distention are necessary to provide adequate increased volume to move pelvic organs about and achieve the necessary visualization and surgical access to the operation site. One form of the laparoscopic port, has three channels along its length. One channel carries a fiber optical cable bundle for transmission of illuminating light and the image for visualization of the working field through the eyepiece. A second channel includes a stopcock or valve for controlling the input of insufflating $CO_2$ gas. A third channel is provided for the withdrawal of gas and smoke. Other forms of laparoscopic tubes may contain one or two channels.

Various procedures for implacing laparoscopic ports are employed. In one procedure, a small incision is made in the skin of the patient, in the navel or just below the navel, and a large hollow needle inserted into the abdominal cavity. The abdominal cavity is then distended with carbon dioxide gas passed through the needle using an abdominal insufflator raising the pressure to the equivalent of 15 to 20 mm of Hg. When the abdomen is properly distended, the needle is removed and a trochar is inserted through the same small incision used for the large needle. The trochar is then removed leaving a sleeve for the insertion of a laparoscope. To this point, this is referred to as a "single puncture" technique and typically is used for diagnostic laparoscopy. Where a patient is undergoing laser surgery, usually one or two additional small incisions are made in the lower abdomen above the groin on either side. These incisions then are used for the insertion of additional ports for the necessary instruments including the laser beam carrying tube or cautery device.

The present invention can best be understood by reference to the drawings and the descriptions below.

Figure 1:
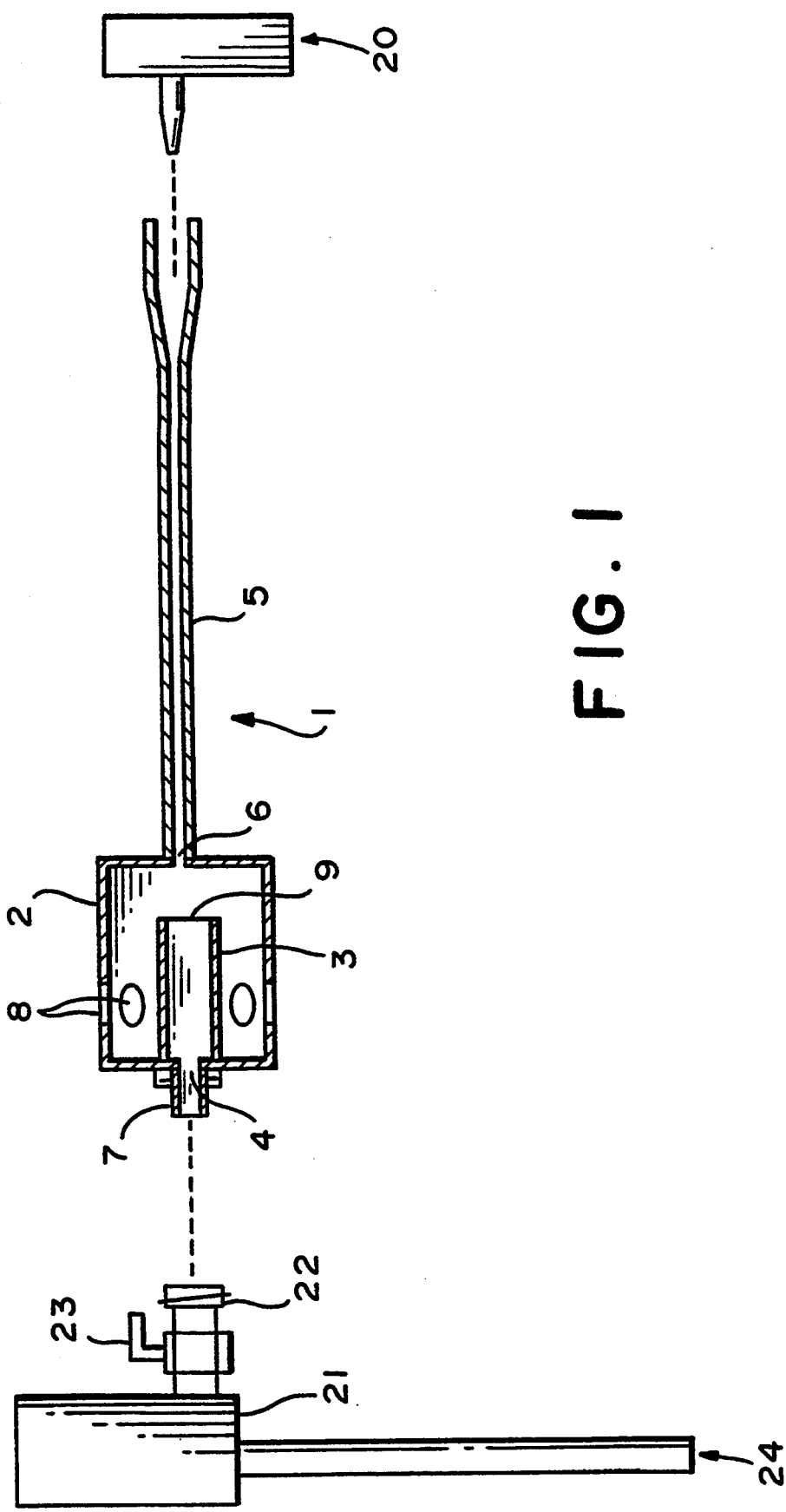
FIG. 1, is a detailed cross sectional diagram of a first embodiment of an air quality enhancement device.

Referring to FIG. 1, an air quality enhancement device 1, a laparoscopic assembly 24 and a vacuum pump 20 are graphically illustrated. The device 1 comprises a rigid hollow envelope 2 having a plurality of apertures 8 located toward a forward or upstream region of the envelope 2. The apertures are preferably in a substantially concentric arrangement to allow ingress of air from the surrounding atmosphere in a substantially symmetrical flow. Although a plurality of apertures 8 is preferred, such as about six to eight apertures, it is within the scope of the present invention to employ a single aperture at the forward region of the hollow envelope 2.

The hollow envelope 2 contains a first opening 4 located at a forward region of the envelope, and a second opening 6 located at a rearward region of the envelope. A fluid flow tube 3 is disposed within the envelope 2. The fluid flow tube 3 is in a sealing arrangement with the envelope 2 at the first opening 4. The tube 3 extends into the interior of the hollow envelope 2 to a rearward or downstream region thereof. The tube 3 has openings at both ends. As indicated above, one opening is identical with opening 4 and the other opening, hereinafter called the interior opening, is indicated as by 9. The interior opening 9 is in a rearward or downstream region of the hollow envelope so that the flow of smoke from a patient cavity does not exit the hollow envelope 2 via the apertures 8. The smoke flows from the patient cavity, through the device 1 and to the vacuum pump 20. The length of the fluid flow tube 3 is at least as long as the distance from opening 4 to a point immediately downstream from apertures 8. In a preferred embodiment the tube 3 extends into the rearward region of hollow envelope 2.

A first connecting structure 7 is located at the first opening 4 of the envelope 2. The connecting structure 7 is in a sealing arrangement with the envelope 2 and can be an integral part of the fluid flow tube 3. In a preferred embodiment the connecting structure 7, the hollow envelope 2 and the fluid flow tube 3 are incorporated in a single one-piece molded device. In an alternative embodiment, the connecting structure 7 and the tube 3 are incorporated in a one-piece molded device, the device being then secured in a sealing arrangement to the envelope 2.

The first connecting structure 7, preferably comprising a Luer lock, easily attaches and detaches the air quality enhancement device 1 to a laparoscopic assembly 24 at a vent opening 22 disposed on a side of a laparoscopic port 21. The vent opening 22 can have a valve 23 associated therewith.

In a method aspect of the present invention, the valve 23 associated with the laparoscopic vent opening 22 can be opened in a continuous fashion once the present device is attached to the laparoscopic assembly 24. The ingress of atmospheric air through the apertures 8 prevents suction from being transmitted along the path of the laparoscopic port 21 even under full vacuum pressure. A flow of laser smoke and other contaminants, such as vaporized tissue and live viruses, passes from the patient cavity, through the laparoscopic port 21, out of the laparoscopic vent opening 22, and into the air quality enhancement device 1 where the flow combines With air from the atmosphere drawn in through the apertures to form a mixed stream of smoke contaminant and air. It is also within the scope of the present invention to adjust the vent valve 23 to obtain a removal of laser smoke and other contaminants from the patient cavity at selected intervals. The mixed stream passes through a second connecting means 5 which can be made of a material such as flexible plastic tubing and enters the conventional hospital vacuum system as represented by vacuum pump 20.

Figure 2:
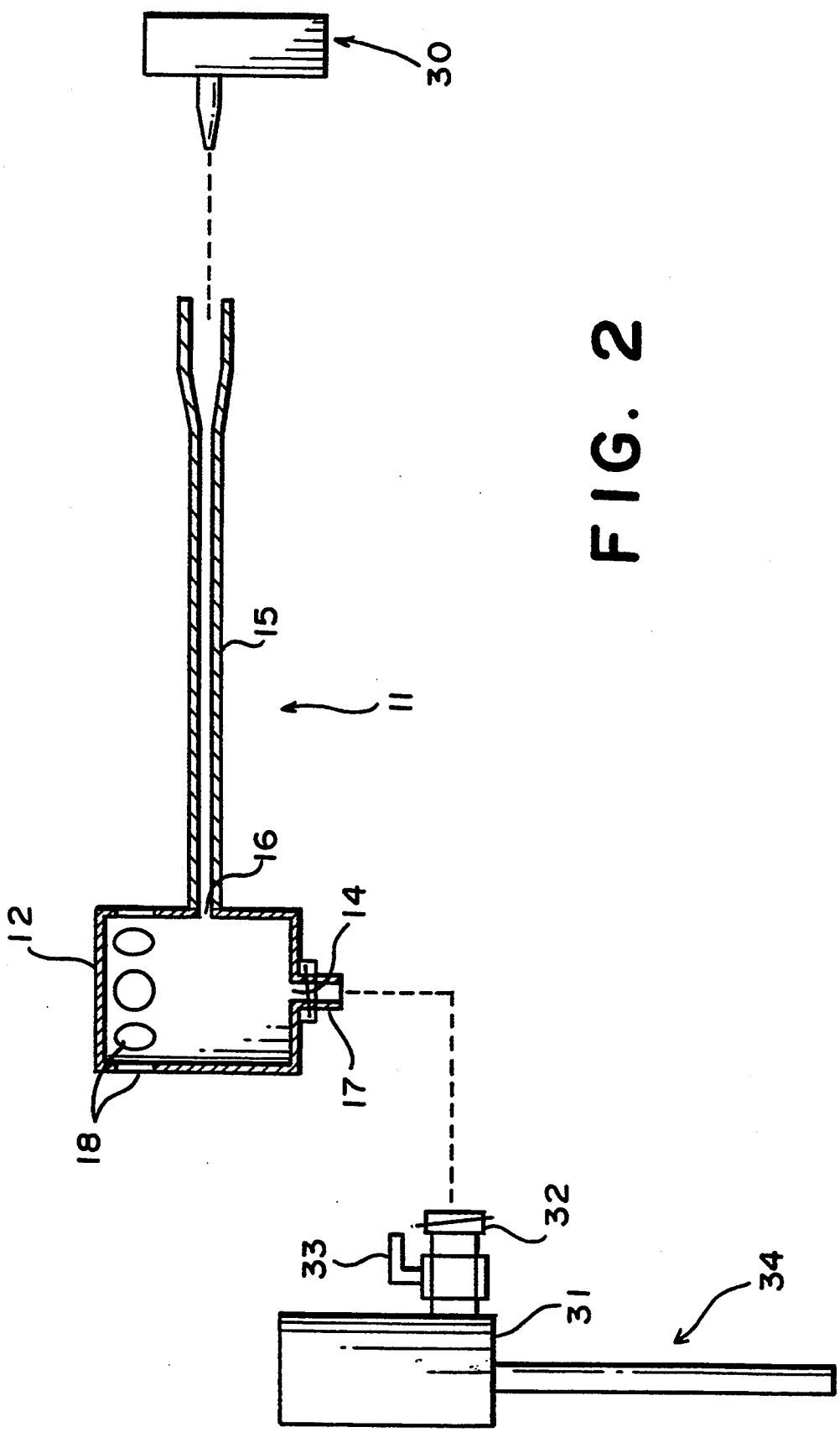
FIG. 2 is a detailed cross sectional diagram of an alternative embodiment of an air quality enhancement device.

Referring to FIG. 2, an alternative design for an air quality enhancement device 11 is graphically illustrated. The device 11 comprises a rigid hollow envelope 12 having a plurality of apertures 18 located at one end of the envelope 12. The apertures are preferably in a substantially concentric arrangement, which provides for a drawing-in of air essentially completely circumferentially about the vertical axis of envelope 12 such that the generation of objectional noise by ingress air is essentially eliminated. Although a plurality, about six to eight, apertures is preferred, it is within the scope of the present invention to employ a single aperture in the envelope 12.

A first opening 14 is located at the other end of the envelope 12. A second opening 16 is located at a position substantially between the apertures 18 and the opening 14 of envelope 12. By "substantially between" is meant the substantially middle region of the hollow envelope 12.

A first connecting structure 17 is located at the first opening 14 and is in a sealing arrangement with the hollow envelope 12. In a preferred embodiment, the connecting structure 17 and the hollow envelope 12 are incorporated in a single one-piece molded device. Preferably the first connecting structure 17 comprises a Luer lock. The Luer lock easily attaches and detaches the air enhancement device 11 to a laparoscopic assembly 34 at vent opening 32, which can include a valve 33, disposed on a side of a laparoscopic port 31. Once again, with the alternative design represented by FIG. 2 the valve 33 associated with the laparoscopy vent valve opening 32 can remain in a continuous open position when connected to the air enhancement device. There is no damage to internal organs because ingress air through apertures 18 prevents any suction force across the path of the laparoscopy port 31 which extends into the patient cavity, even when full vacuum pressure is applied.

A second connecting structure 15 is in a sealing arrangement with envelope 12 at the second opening 16. In a preferred embodiment, the second connecting structure 15 comprises a flexible plastic tube which can be made from any suitable flexible plastic material. It is convenient to use a tubing which is translucent or transparent as opposed to an opaque tubing, although an opaque tubing may be used. The second connecting structure 15 is attached to a vacuum pump 30 by suitable means.

Preferably the air quality enhancement devices represented by FIGS. 1 and 2 can be integrally molded out of plastic so as to make the cost sufficiently low that the assembly can be disposable. The use of such a disposable unit minimizes the possibility of contamination. The units employed in the present invention are preferably transparent, thereby allowing the medical personnel to readily observe whether debris is accumulating at any point in the tubes. The units are constructed of any of the plastic compositions conventionally known in the plastics art for similar applications. Preferably both the hollow envelope and fluid flow tube comprise a rigid plastic material such as polyvinyl chloride or polyester resin. The inside surfaces have a smooth configuration thereby reducing any possibility that debris will build up, obstructing the flow of air through the system.

The present invention includes a laparoscopic assembly comprising a port, a vent valve and a venting opening in combination with an air quality enhancement device. In one embodiment the laparoscopic assembly and air quality enhancement device are combined in a one-piece molded article. In an alternative embodiment, the air enhancement device is detachable from the laparoscopic assembly. The device can have the design as represented by FIG. 1 or FIG. 2.

An evacuation method is disclosed for removing laser smoke or electrocautery smoke from an operation site in a patient cavity during laparoscopy. The method comprises inserting a laparoscopic port having a valve means on a side thereof into a patient cavity, connecting the valve means to an easily detachable air quality enhancement device, and connecting the air quality enhancement device to a vacuum pump suction line. Laparoscopic surgery is then performed. The valve means is adjusted to provide either a continuous or discontinuous suction for withdrawal of smoke and other contaminants from the patient cavity. A smoke-free environment for surgeons and patient is thus provided.

The air quality enhancement device useful in the evacuation method comprises a hollow envelope having at least one aperture disposed at a forward region thereof, a first opening through a wall of the envelope at a forward region thereof, and a second opening through the wall of the hollow envelope at a rearward region thereof. A fluid flow tube is sealed to the first opening and extends into the interior of the hollow envelope. The tube has openings at both ends including a primary opening corresponding to the first opening of the hollow envelope for ingress of smoke and other contaminants, and a secondary opening within the interior of the hollow envelope and at a rearward region thereof. A first connecting means is located at the first opening of the hollow envelope and operatively attaches the air quality enhancement device to a valve means positioned on a side of a laparoscopic port. A second connecting means is located at the second opening of the hollow envelope and operatively attaches the air quality enhancement device to a vacuum pump suction line.

An alternative design for the air quality enhancement device to be employed in the evacuation method, which can be used to remove laser smoke or electrocautery smoke, is represented in FIG. 2. The device comprises a hollow envelope having a plurality of apertures located at a rearward region thereof, a first opening through a wall of the hollow envelope at a forward region thereof, and a second opening through the wall of the hollow envelope at a substantially middle region thereof. A first connecting means is located at the first opening of the hollow envelope and operatively attaches the air quality enhancement device to a valve means positioned on a side of a laparoscopic port. A second connecting means is located at the second opening of the hollow envelope and operatively attaches the air quality enhancement device to a vacuum pump suction line.

Many equivalent modifications will be apparent from a reading of the above to those skilled in the art without a departure from the inventive concept which is limited and defined only by the appended claims.

What is claimed is:

1. An air quality enhancement device for removal of electrocautery or laser smoke from a patient cavity comprising:
   a hollow envelope having a forward, middle and rearward region further having a plurality of apertures disposed at the forward region thereof, a first opening means formed in said hollow envelope at the forward region thereof, and a second opening means formed in said hollow envelope at the rearward region thereof,
   a fluid flow tube sealed to the envelope at the first opening means and extending into the interior of the hollow envelope, said tube having openings at both ends, one opening identical with the first opening means of the hollow envelope for ingress of smoke and other contaminants, and an interior opening within the hollow envelope and at the rearward region thereof;
   a first connecting means located at the first opening means of the hollow envelope for operatively attaching the air quality enhancement device to a laparoscopic assembly; and
   a second connecting means located at the second opening means of the hollow envelope for operatively attaching the air quality enhancement device to a vacuum pump suction line.

2. A device according to claim 1 wherein the hollow envelope comprises a rigid plastic material.

3. A device according to claim 1 wherein the fluid flow tube comprises a rigid plastic material.

4. A device according to claim 1 wherein the first connecting means comprises a Luer Lock.

5. A device according to claim 1 wherein the second connecting means comprises a flexible plastic tube.

6. In combination, a laparoscopic assembly and an air quality enhancement device the device comprising:
   a hollow envelope having a forward, middle and rearward region further having a plurality of apertures at the forward region thereof, a first opening means through a wall of the hollow envelope at the forward region thereof, and a second opening means through the wall of the hollow envelope at the rearward region thereof,
   a fluid flow tube sealed to the first opening means and extending into the interior of the hollow envelope, said tube having openings at both ends, one opening corresponding to the first opening means of the hollow envelope for ingress of smoke and other contaminants, and an interior opening within the hollow envelope and at the rearward region thereof;
   a first connecting means located at the first opening means of the hollow envelope and operatively attaching the air quality enhancement device to a laparoscopic assembly; and
   a second connecting means located at the second opening means of the hollow envelope for operatively attaching the air quality enhancement device to a vacuum pump suction line.

7. A combination according to claim 6 wherein the air quality enhancement device is detachable from the laparoscopic assembly.

8. An evacuation method for removing laser smoke from an operation site in a patient cavity during laser laparoscopic surgery comprising the steps of:

inserting a laparoscopic port having a valve means on a side thereof into a patient cavity;

connecting the valve means to an easily detachable air quality enhancement device as described below;

connecting the air quality enhancement device to a vacuum pump suction line, and performing laparoscopic surgery and adjusting the valve means to provide either a continuous or discontinuous suction for withdrawal of smoke and other contaminants from the patient cavity thereby providing a smoke-free environment for surgeons;

said air quality enhancement device comprising:

(1) a hollow envelope having a forward, middle and rearward region further having at least one aperture disposed at the forward region thereof, a first opening means through a wall of the hollow envelope at the forward region thereof, and a second opening means through the wall of the hollow envelope at the rearward region thereof;

(2) a fluid flow tube sealed to the first opening means and extending into the interior of the hollow envelope, said tube having openings at both ends, one opening corresponding to the first opening means of the hollow envelope for ingress of smoke and other contaminants, and an interior opening within the hollow envelope and at the rearward region thereof, (3) a first connecting means located at the first opening means of the hollow envelope for operatively attaching the air quality enhancement device to a valve means positioned on a side of a laparoscopic port; and (4) a second connecting means located at the second opening means of the hollow envelope for operatively attaching the air quality enhancement device to a vacuum pump suction line.

* * * * *